(12) United States Patent
Thome et al.

(10) Patent No.: US 9,579,168 B2
(45) Date of Patent: Feb. 28, 2017

(54) MULTIFUNCTIONAL PROSTHETIC COMPONENT AND ITS METHOD OF USE

(71) Applicant: JJGC INDUSTRIA E COMERCIO DE MATERIAIS DENTARIOS S.A., Curitiba (BR)

(72) Inventors: Geninho Thome, Curitiba (BR); Alexsander Luiz Golin, Curitiba (BR); Ilderaldo Jose Lucca, Curitiba (BR); Almir Borges Zvetz, Curitiba (BR); Felix Andreas Mertin, Curitiba (BR)

(73) Assignee: JJGC INDUSTRIA E COMERCIO DE MATERIAIS DENTARIOS S.A., Curitiba (BR)

( * ) Notice: Subject to any disclaimer, the term of this patent is extended or adjusted under 35 U.S.C. 154(b) by 192 days.

(21) Appl. No.: 14/519,717

(22) Filed: Oct. 21, 2014

(65) Prior Publication Data

US 2015/0111175 A1   Apr. 23, 2015

(30) Foreign Application Priority Data

Oct. 22, 2013   (BR) .............................. 102013027205

(51) Int. Cl.
*A61C 8/00*   (2006.01)

(52) U.S. Cl.
CPC .......... *A61C 8/0028* (2013.01); *A61C 8/0001* (2013.01); *A61C 8/0048* (2013.01); *A61C 8/0087* (2013.01); *A61C 8/0089* (2013.01); *A61C 8/0068* (2013.01)

(58) Field of Classification Search
CPC ... A61C 8/0028; A61C 8/0001; A61C 8/0048; A61C 8/0087–8/0089
USPC .................................................. 433/172–174
See application file for complete search history.

(56) References Cited

U.S. PATENT DOCUMENTS

| | | | | | |
|---|---|---|---|---|---|
| 4,758,161 | A | * | 7/1988 | Niznick | A61C 8/0053 433/173 |
| 4,790,753 | A | * | 12/1988 | Fradera | A61C 8/0022 433/174 |
| 5,049,073 | A | * | 9/1991 | Lauks | A61C 8/0018 433/169 |
| 5,281,140 | A | * | 1/1994 | Niznick | A61C 8/005 433/172 |
| 5,312,254 | A | * | 5/1994 | Rosenlicht | A61C 8/005 206/63.5 |
| 5,564,924 | A | * | 10/1996 | Kwan | A61C 8/0001 433/173 |

(Continued)

FOREIGN PATENT DOCUMENTS

WO   2006/088680 A2   8/2006

*Primary Examiner* — Alvin Stewart
(74) *Attorney, Agent, or Firm* — Banner & Witcoff, Ltd.

(57) ABSTRACT

In one aspect, a multi-use prosthetic component is provided. In certain examples, the component comprises a prismatic head, external marks and internal hexagon for indexing, fitting and orientation of the assembly. In another aspect, a dental implant system is provided, where in certain examples the system includes a covering cylinder, a plastic cover, a set screw and an implant with an external hexagon, which allows for, in addition to the function as a conventional assembler, capturing the implant in the packaging, shipping and installation in the bone tissue, application of torque, impression coping, a prosthetic pillar indexed to the implant device, and 3D orientation during surgery.

16 Claims, 7 Drawing Sheets

(56) References Cited

U.S. PATENT DOCUMENTS

| | | | | |
|---|---|---|---|---|
| 5,620,323 A * | 4/1997 | Bressman | A61C 8/0022 | 433/174 |
| 5,681,167 A * | 10/1997 | Lazarof | A61C 8/0001 | 433/173 |
| 6,039,568 A * | 3/2000 | Hinds | A61C 8/0036 | 433/173 |
| 6,159,010 A * | 12/2000 | Rogers | A61C 8/0048 | 433/172 |
| 6,227,856 B1 * | 5/2001 | Beaty | A61C 8/0001 | 433/172 |
| 6,287,116 B2 * | 9/2001 | Lazzara | A61C 8/0001 | 433/172 |
| 6,287,117 B1 * | 9/2001 | Niznick | A61C 8/0087 | 433/173 |
| 6,290,499 B1 * | 9/2001 | Lazzara | A61C 8/008 | 433/172 |
| 6,375,465 B1 * | 4/2002 | Engman | A61C 8/0022 | 433/172 |
| 6,454,567 B1 * | 9/2002 | Carchidi | A61C 8/0089 | 433/141 |
| 6,824,386 B2 * | 11/2004 | Halldin | A61C 8/0001 | 433/173 |
| 6,981,873 B2 * | 1/2006 | Choi | A61C 8/0025 | 433/173 |
| 7,014,464 B2 * | 3/2006 | Niznick | A61C 8/0001 | 433/173 |
| 7,137,816 B2 * | 11/2006 | Gervais | A61C 8/0001 | 433/173 |
| 7,300,284 B2 * | 11/2007 | Linder | A61C 8/0089 | 433/172 |
| 7,632,095 B2 * | 12/2009 | Ostman | A61O 5/08 | 433/172 |
| 7,699,613 B2 * | 4/2010 | Niznick | A61C 8/0001 | 433/174 |
| 7,785,107 B2 * | 8/2010 | Niznick | A61C 8/0022 | 433/173 |
| 8,506,296 B2 * | 8/2013 | Bassett | A61C 8/0001 | 433/173 |
| 8,632,336 B2 * | 1/2014 | Rossler | A61C 8/0001 | 433/174 |
| 8,727,774 B1 * | 5/2014 | Arendt | A61C 8/0022 | 433/163 |
| 8,794,966 B2 * | 8/2014 | Hung | A61C 8/0089 | 433/173 |
| 8,944,818 B2 * | 2/2015 | Robb | A61C 8/008 | 433/172 |
| 8,951,042 B2 * | 2/2015 | Buchegger | A61C 8/0068 | 433/173 |
| 9,125,710 B2 * | 9/2015 | Bassett | A61C 8/0068 | |
| 2002/0064758 A1 * | 5/2002 | Lee | A61C 8/0001 | 433/172 |
| 2002/0106610 A1 * | 8/2002 | Hurson | A61C 8/0001 | 433/173 |
| 2002/0127517 A1 * | 9/2002 | Morgan | A61C 8/0001 | 433/173 |
| 2003/0054319 A1 * | 3/2003 | Gervais | A61C 8/0001 | 433/173 |
| 2003/0082498 A1 * | 5/2003 | Halldin | A61C 8/0001 | 433/173 |
| 2003/0082499 A1 * | 5/2003 | Halldin | A61C 8/0001 | 433/173 |
| 2003/0224331 A1 * | 12/2003 | Kumar | A61C 8/005 | 433/173 |
| 2006/0003290 A1 * | 1/2006 | Niznick | A61C 8/0075 | 433/174 |
| 2006/0078847 A1 * | 4/2006 | Kwan | A61C 8/0001 | 433/174 |
| 2006/0084035 A1 * | 4/2006 | Volz | A61C 8/0012 | 433/173 |
| 2006/0172257 A1 * | 8/2006 | Niznick | A61C 8/0022 | 433/173 |
| 2006/0216673 A1 * | 9/2006 | Park | A61C 8/0022 | 433/173 |
| 2007/0059666 A1 * | 3/2007 | Zickman | A61C 8/005 | 433/173 |
| 2007/0072150 A1 * | 3/2007 | Mansueto | A61C 8/0022 | 433/174 |
| 2007/0099152 A1 * | 5/2007 | Busch | A61C 8/0001 | 433/173 |
| 2007/0148620 A1 * | 6/2007 | Kim | A61C 8/0048 | 433/172 |
| 2008/0153062 A1 * | 6/2008 | Beaty | A61C 8/0001 | 433/173 |
| 2008/0241793 A1 * | 10/2008 | Collins | A61C 8/0006 | 433/174 |
| 2010/0099058 A1 * | 4/2010 | Wang | A61C 13/0004 | 433/173 |
| 2010/0159417 A1 * | 6/2010 | Whipple | A61C 8/0075 | 433/172 |
| 2010/0196851 A1 * | 8/2010 | Konig | A61C 8/0066 | 433/173 |
| 2010/0285427 A1 * | 11/2010 | Hung | A61C 8/0089 | 433/174 |
| 2011/0117522 A1 * | 5/2011 | Verma | A61C 8/0022 | 433/174 |
| 2011/0123947 A1 * | 5/2011 | Borel | A61C 8/0018 | 433/172 |
| 2011/0306014 A1 * | 12/2011 | Conte | A61C 8/005 | 433/173 |
| 2013/0004916 A1 * | 1/2013 | Bellanca | A61C 8/0018 | 433/173 |
| 2016/0015485 A1 * | 1/2016 | Gonella | A61C 8/0054 | 433/173 |

\* cited by examiner

MULTIFUNCTIONAL PROSTHETIC COMPONENT AND ITS METHOD OF USE

CROSS REFERENCE TO RELATED APPLICATION

This application claims priority under 35 U.S.C. §119 to Brazilian patent application BR 102013027205-1, filed Oct. 22, 2013, the disclosure of which is incorporated herein by reference.

BACKGROUND

In the field of dental implants, to assist in the installation of the implant the use of either external hex or the internal hex interfaces is are already widely disclosed, as well as the use of assemblers.

Although there are options that obviate the need to use assemblers, these artifacts are part of the dental activity when it comes to the installation of dental implants, the most common practice is to use a tool that captures the implant from its packaging, which carries the implant to the bone tissue and installs in its position of use.

The document WO2006/088680 presents a one-piece, screw-receiving, externally-threaded endosseous dental implant that includes a part with an external thread and, at its proximal end, an unthreaded, cylindrical part including a retentive groove for engaging a complementary transfer component or comfort cap; a one or two piece screw-receiving implant pillar for attachment to a one or two piece implant, including a retentive groove for engaging a complementary transfer component or comfort cap; and a fixture mount for insertion in a one-piece implant, that can be sectioned with the distal end used to extend the implant height. Document U.S. Pat. No. 7,785,107 presents endosseous dental implants which includes external threads and in an internal passage within the interior of the implant body, a bevel guide, surfaces for engaging octagonal notches engaging surfaces for hex tools that are distally positioned, internal distal threads both hexagonal and octagonal surfaces and coupling and assembly devices, including male projections for attaching the surfaces for hex coupling tools within the implants.

SUMMARY

This innovation belongs to the field of dental medicine, more specifically dental implants. The following presents a simplified summary of the present disclosure in order to provide a basic understanding of some aspects of the present disclosure. This summary is not an extensive overview of the present disclosure. It is not intended to identify key or critical elements of the present disclosure or to delineate the scope of the present disclosure. The following summary merely presents some concepts of the present disclosure in a simplified form as a prelude to the more detailed description provided below.

In the sense of developing known technologies, after a thorough analysis of the state of the art, there is a perceived gap in relation to a particular implant system, which will offer many of the features necessary to implantology.

Therefore, an innovation is proposed that, in certain aspects, constitutes a dental implant system or components thereof. In certain examples, a system is provided, the system comprising a dental implant, endowed with an external hexagon, a multi-use prosthetic component, a set screw for fixing the system and a cylinder for making a dental prosthesis. In some examples, the multifunctional prosthetic component includes an internal hex multi-use prosthetic component endowed on the internal hexagon, wherein the said prosthetic component has multiple functions, including being used to capture the packaging, transportation, installation and application of torque, impression coping, providing an indexed prosthetic pillar to the implant, as well as a 3D orientation device during the surgical procedure. Such apparatuses are also associated with methods of use, which take advantage of the features and benefits, including those offered by the multi-functional component.

When compared to the relevant documents described above, it can be seen that the protection claimed by the WO2006/088680 is unlike the proposed innovation, an internal implant-pillar connection. And the patent U.S. Pat. No. 7,785,107 claims, unlike the innovation, a geometry that does not include indexing or the multi-functionality that is proposed here.

In this way, embodiments of the innovation have advantages over the prior state of the art, including, for example:
  Convenience: the products that are essential to the technique are combined in a single package;
  Value: all components are compatible with an entire line of components that have an external hexagon; and
  Reduction in the stages of the surgical procedure and transfer of the molding for the manufacture of the prosthesis.

These summary descriptions are merely exemplary. In certain embodiments, the systems and components comprise additional combinations or substitutions. Moreover, any of the features discussed in the exemplary embodiments of one aspect may be features of embodiments of any other aspect discussed herein.

DESCRIPTION OF THE DRAWINGS

Exemplary embodiments of the disclosure will now be described by way of example only and with reference to the accompanying drawings, in which.

In step "B" the uncoupling of the plastic cover can be seen (2) after the molding transfer process, which prevents the entry of molding material into the hole to insert the attachment screw (3).

Step "C" illustrates the section of the multi-use prosthetic component (4) done by a cutting disc, that results in two parts: the prismatic head (4.1) and the prosthetic pillar (4.2) which, after cutting, is again attached to the implant (5) by the attachment screw (3).

In step "D" the cylinder is checked (1) before placing it on the prosthetic pillar (4.2). Step "E" illustrates the cylinder (1) already attached to the prosthetic pillar (4.2).

DETAILED DESCRIPTION

In one aspect, the proposed innovation is a multifunctional prosthetic component. In one example, the multifunctional prosthetic component (4), is endowed with internal hexagon (4F), a set screw system (3) and a cylinder for making a dental prosthesis (1). Specifically, examples of the multi-use prosthetic component (4) provide the innovation in its use in several distinct functions: a) capturing the packaging, transportation, installation and application of torque; b) impression coping; c) prosthetic post indexed to the implant; and d) 3D orientation of the device during the surgical procedure.

In the traditional technique, the implant (5) may be introduced by means of a conventional assembler that is used only for transport to the bone tissue and the application of torque, and is then immediately discarded because it has no further use, therefor providing the adaptation of a conventional prosthetic component.

With the use of certain examples it is proposed that the multi-use prosthetic component (4) has a plastic cover (2) in its upper portion, which has a channel shaped clamp (2B) for the accurate mounting on the multi-use prosthetic component (4) and a cylindrical rod (2A) to allow the fixing on the O-ring (6A) of the installation key (6).

Figure 7:
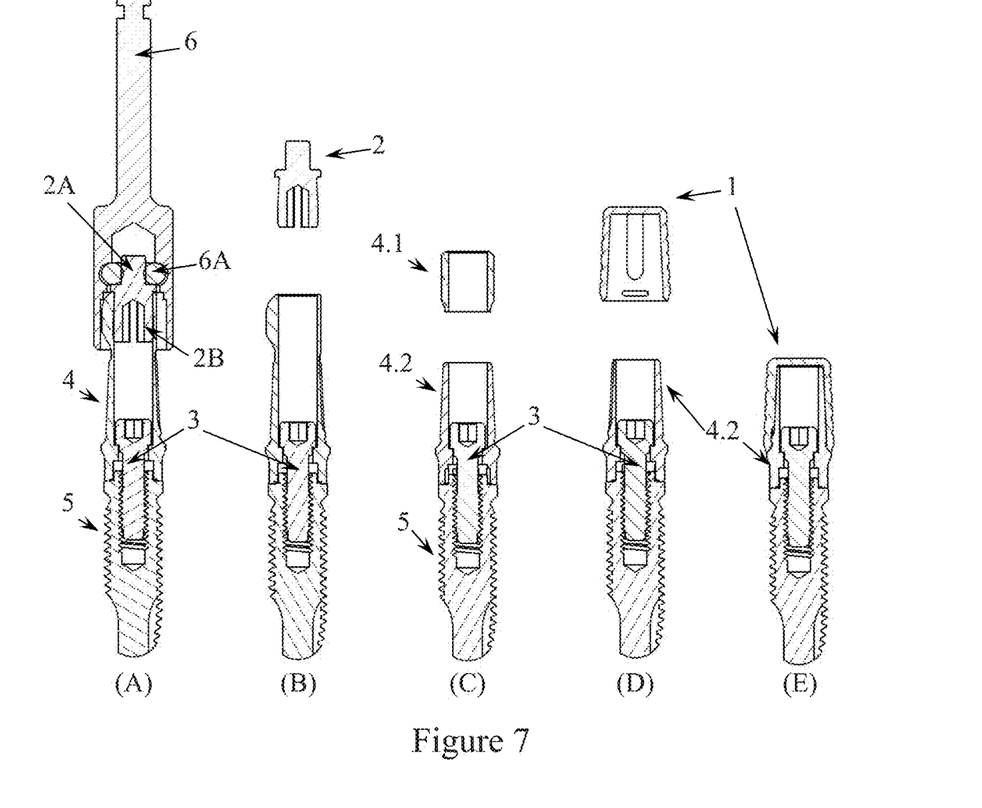
FIG. 7 illustrates the sequence of a use of an example of this innovation, observing that in step "A" the capture system, the O-ring (6A) belonging to the key (6) is attached to the cylindrical rod (2A) of the plastic cover (2) which is attached to the multi-use prosthetic component (4) by means of the clamp-shaped channel (2B) while the multi-use prosthetic component (4) is attached to the implant (5) by the attachment screw (3).

With the aid of the installation key (6), the whole assembly, consisting of the plastic cover (2), the screw (3), the multi-use prosthetic component (4) and the implant (5) is captured at the region of the cylindrical stem (2A) of the plastic cover, allowing its transport to the bone tissue (FIG. 7, "A").

In certain examples, the multi-use prosthetic component (4) presents in its physical configuration a prismatic head (4.1) containing smaller surfaces (4B) with a hexagonal shape, used for the application of torque, as well as larger surfaces (4A), with triangular profile in its cross section, that are used for the 3D orientation, which may also adopt a hexagonal form. Optionally, the faces may have different and compatible shapes, for example, larger faces (4A) associated with a hexagonal prismatic head (4.1) with 12 sides.

Figure 1:
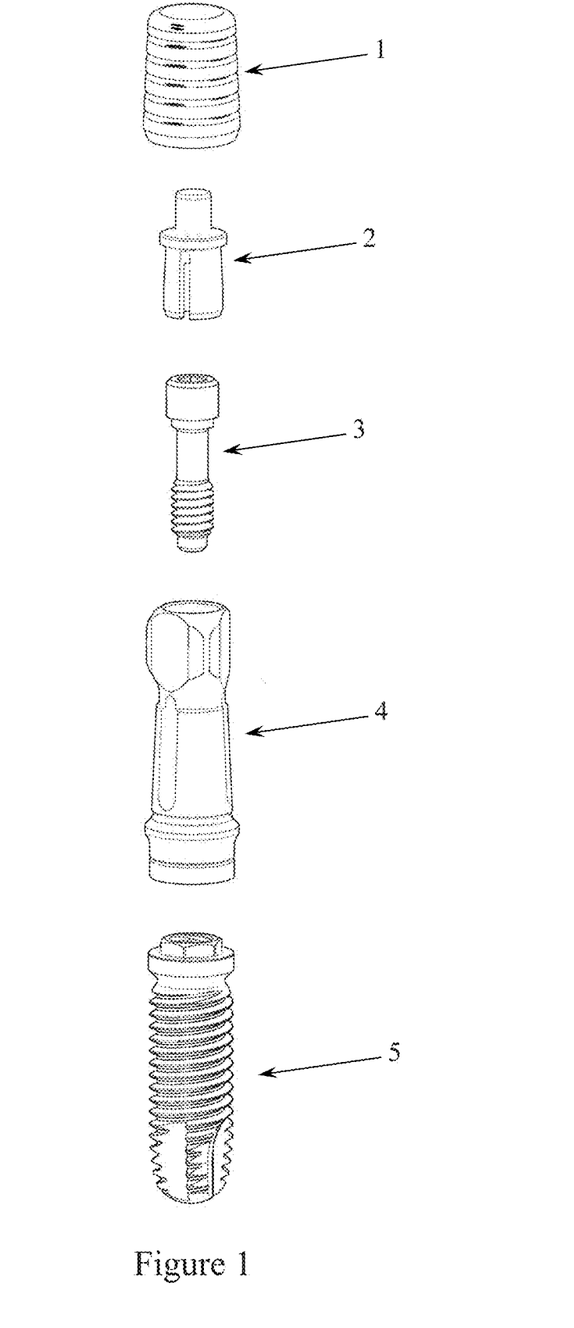
FIG. 1 shows a perspective view of the components of an example the dental implant system proposed here, which illustrates the cylinder (1), the plastic cover (2), the internal screw (3), the multi-use prosthetic component (4) and the implant (5).
Figure 2:
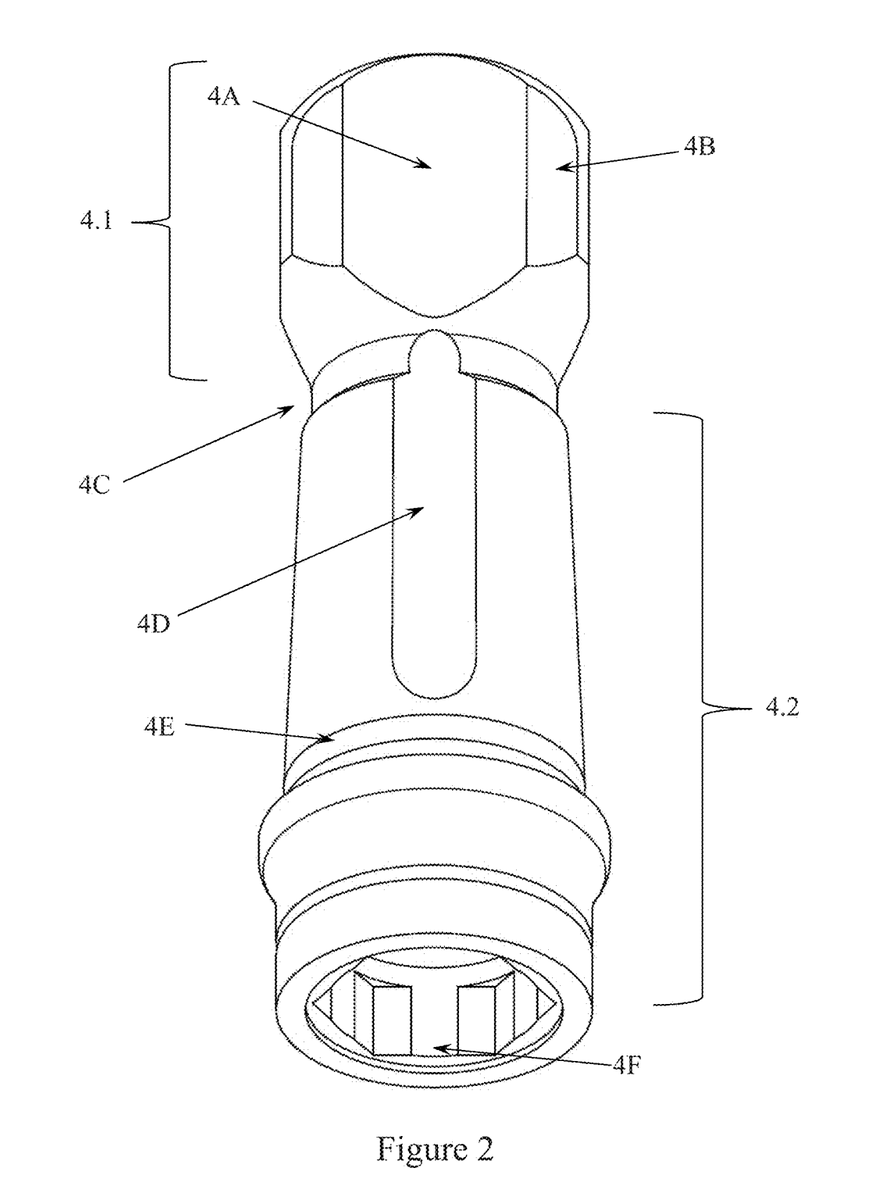
FIG. 2 shows a perspective view of an example of the multi-use prosthetic component, which shows the surfaces (4A and 4B) of the prismatic head (4.1), the guide for the cutting (4C), the section which will become the prosthetic pillar (4.2), the external vertical concave grooves (4D) indexed, or aligned, with the larger surfaces (4A) of the prismatic head (4.1) and the surfaces of the internal hexagon (4F), the channel (4E) for the adaptation of the cylinder (1) with one click, and the internal hexagon (4F).
Figure 3:
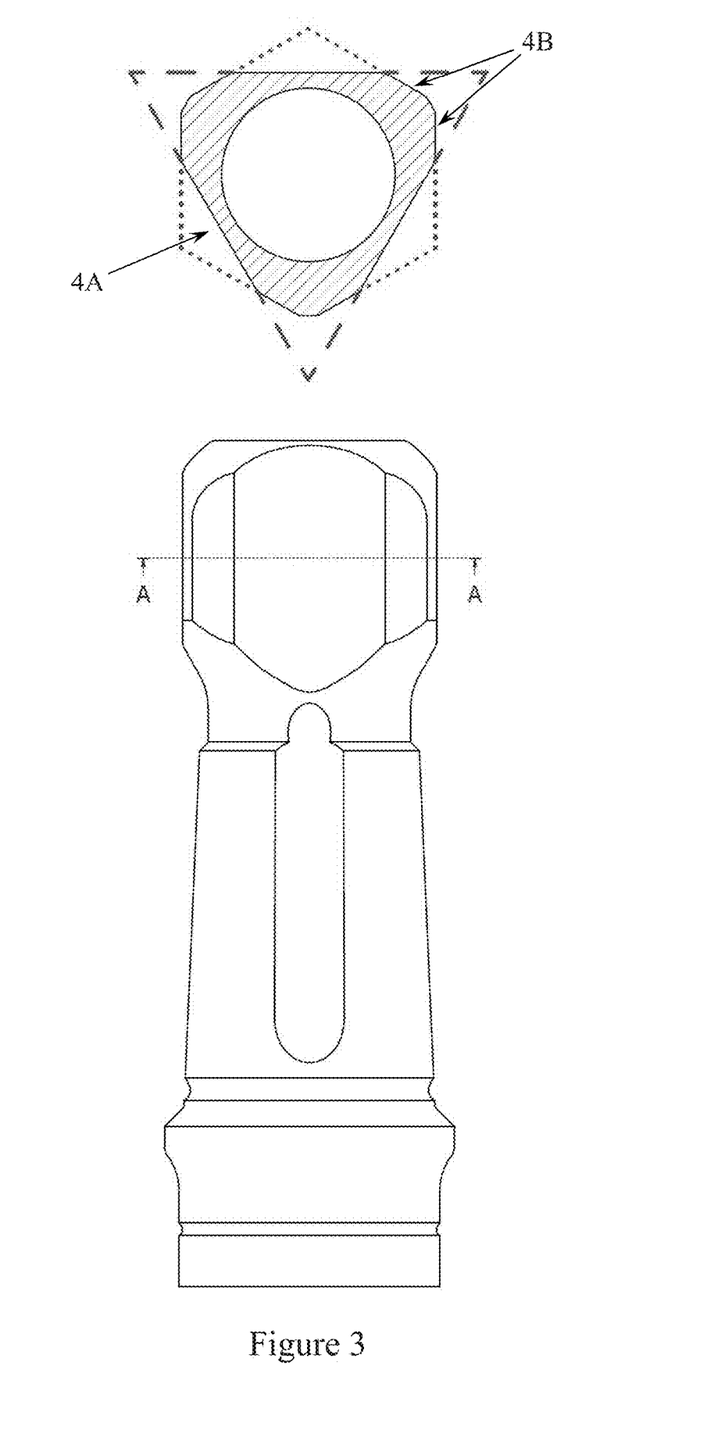
FIG. 3 shows the cross section of an example of the prismatic head (4.1) of the multi-use prosthetic component (4), where one can see a top view in which there are smaller faces (4B) with a hexagonal shape for the application of torque, and the larger surfaces (4A), triangular shaped for three-dimensional orientation, which may also adopt the hexagonal format.
Figure 4:
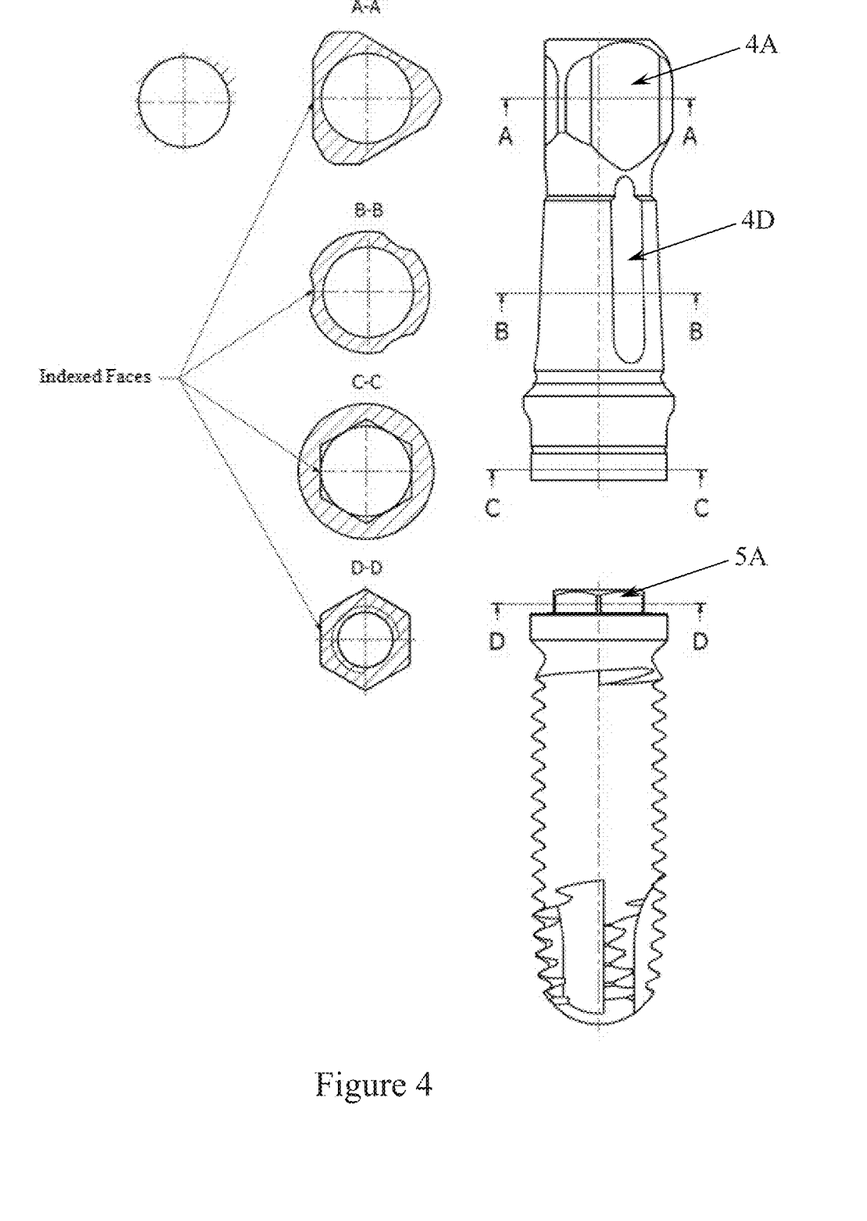
FIG. 4 shows a perspective view of an example of the indexing, or alignment, between the larger surfaces (4A) of the prismatic head (4.1) the external vertical concave grooves (4D) of the prosthetic pillar (4.2) the inner hexagon surfaces (4F) of the multi-use prosthetic component (4) and the external hexagon faces (5A) of the implant (5) which allows the anti-rotational effect and repositioning accuracy of the multi-use prosthetic component (4) on the implant (5).

In certain examples. these surfaces (4A and 4B) of the prismatic head (4.1) are indexed, i.e. aligned, with the inner hexagon surfaces (4F) multi-use prosthetic component (4) that, consequently, are indexed with the surfaces of the external hexagon (5A) of the implant (5). This allows the exact positioning of a prosthetic unit, because it limits the rotation of the multi-use prosthetic component to six (6) precise positions, creating an anti-rotational effect (FIG. 4). In the case described above, for example, there are six possible positions for the allocation of the prosthetic component.

The orientation function of the assembly at the time of installation of the implant (5) is ensured by means of external vertical concave grooves (4D) arranged along the body of the prosthetic pillar (4.2), which are indexed with the larger surfaces (4a) of the prismatic head (4.1). Thus, at least one slot is marked on the body of the prosthetic pillar (4.2) to enable indexing with the larger faces (4A) of the head prism (4.1).

Figure 5:
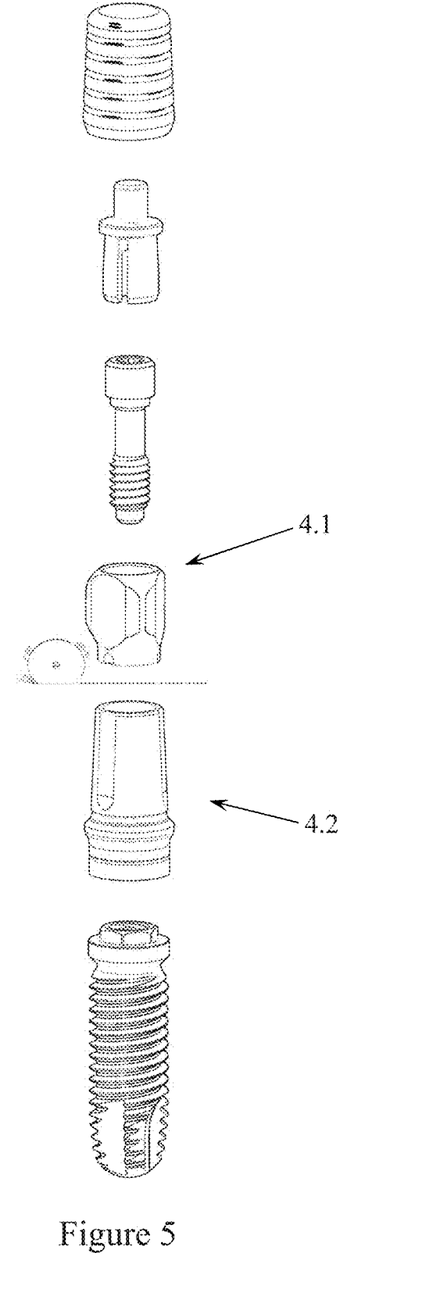
FIG. 5 shows a perspective view of an example of the multi-use prosthetic component (4) after its section by a skilled professional using, for example, a common cutting disk as known in the rehabilitation technique, removing the prismatic head (4.1) and therefore obtaining the prosthetic pillar (4.2).
Figure 6:
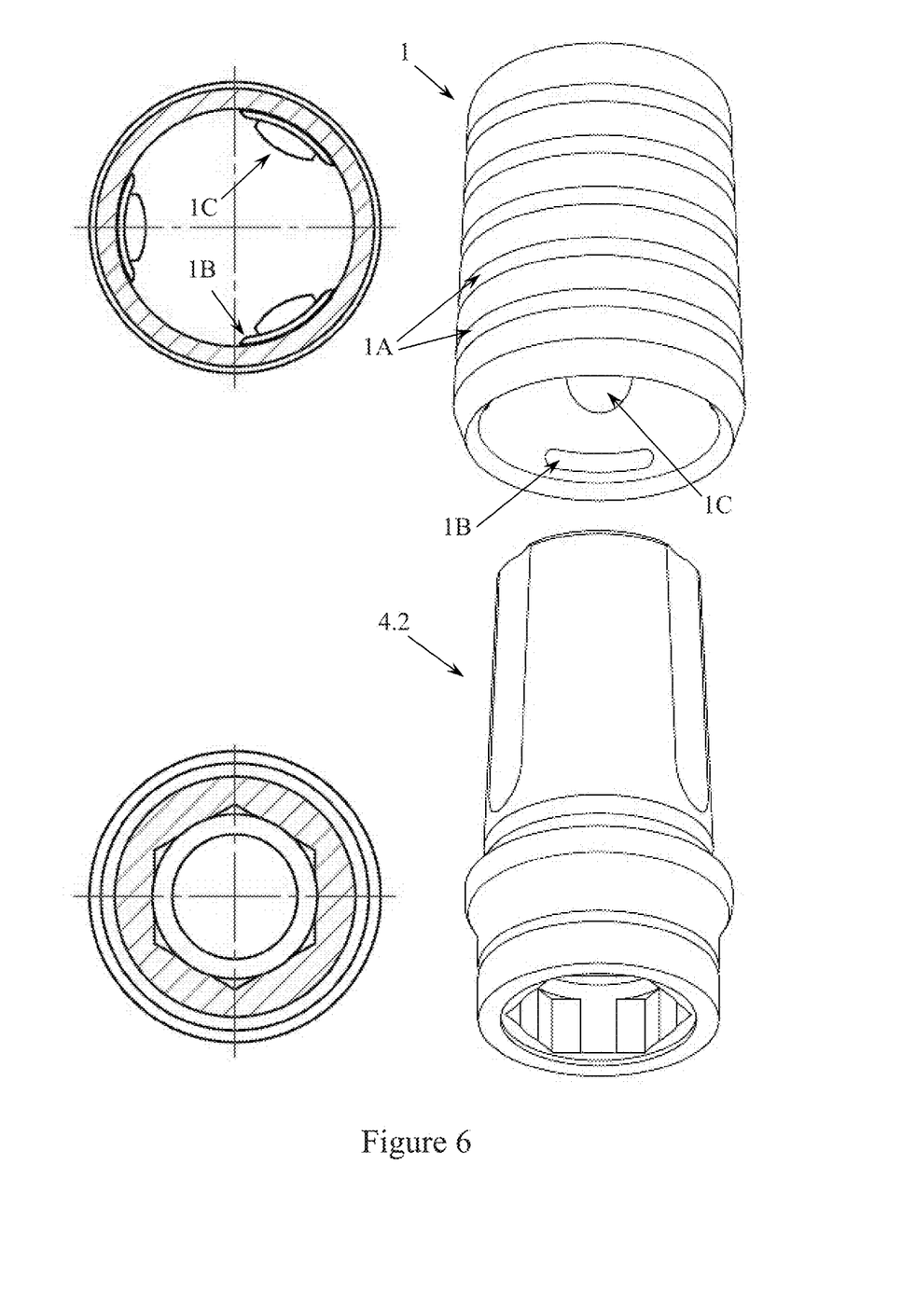
FIG. 6 demonstrates an example of the cylinder (1) on the prosthetic pillar (4.2) and the respective views of slices perpendicular to the longitudinal axes, which show external grooves (1A) for retention of the resin which will be supplied with the prosthesis, the internal protrusions (1B) for engagement with the prosthetic pillar (4.2) with a click, as with the external vertical concave grooves of the pillar that may accept internal convex vertical ridges of the cylinder (1C) for guidance in the positioning of the prosthetic pillar (4.2) and the anti-rotational fitting of the prosthesis.

The multi-use prosthetic component (4) has a groove (4C) below the prismatic head (4.1), which guides the skilled professional to perform the cutting, with a common use disc that is known in the rehab area (FIG. 5) that will transform the multi-use prosthetic component (4) in a prosthetic pillar (4.2).

The presence of an attachment screw (3) determines the attachment of the multi-use prosthetic component (4) on the implant (5), enabling it to be used as a prosthetic pillar (4.2). As a prosthetic pillar (4.2), the multi-use prosthetic component may be used as 3D orientation device for installing more than one implant during the same surgical procedure.

However, the multi-use prosthetic component (4) has a circular channel (4D) above the prosthetic base plate, where the cylinder (1) is fitted with only one click, ensuring safety when adapting the crown.

The cylinder (1), in turn, has an internal projection (1B) for the exact fitting of the prosthetic pillar (4.2) with a click, besides the external grooves (1A) for the retention of the resin that will be supplied with the prosthesis. There are also internal convex vertical ridges (1C) for guidance when locating the prosthetic pillar (4.2).

The multi-use prosthetic component (4) allows one to carry out the impression transferring the implant (5), making the technique easier due to the surfaces on the (4A and 4B) prismatic head (4.1), minimizing the risk of errors in the orientation of the final prosthesis.

Moreover, the presence of the plastic cover (2) provides protection of the internal portion of the multi-use prosthetic component (4) during the transfer process of the molding because it prevents the entry of molding material, facilitating the access of the fixing screw (3).

In summary, examples of the component (4) enable the optimization of the technical installation of dental implants, adopting the multifunctional prosthetic component (4) the association of the function of a conventional assembler with at least one of the additional functions of capture, transport, installation, application of torque; transfer molding; indexed abutment to the implant, as well as three-dimensional orientation device.

This configuration of the multifunctional prosthetic component (4) establishes a method for the specific use, able to enjoy the features offered by the artifact. Thus, in an example scenario of everyday use for the use of implant (5), an installation key may be used (6) to remove the component (4) from packaging, where the O-ring (6A) of the key (6) is coupled in the cylindrical rod (2A) of the plastic cover (2) which is fixed to the multifunctional prosthetic component (4) by means of the clamp-shaped channel (2B) while the multifunctional prosthetic component (4) is attached to the implant by the fixing screw (3). This entire cover assembly (2), multi-functional prosthetic component (4) and the implant (5) is removed from the package and taken to the bone tissue with the key (6), which initiates the torque application on the smaller faces (4B) of prismatic head (4.1) of the multifunctional prosthetic component (4). The completion of the insertion of the implant (5) continues by way of a connection coupled to a ratchet torque wrench, also supported on the smaller faces (4B) of the prismatic head (4.1), allowing for the exact fixing of the assembly.

After completion of the installation of the implant (5), the dentist will perform the process of transfer molding, still with the plastic cover (2) in position, preventing the entry of molding material in the internal portion of the multifunctional prosthetic component (4), and the screw hole (3).

After this process, the practitioner removes the multifunctional prosthetic component (4) by unscrewing it from the implant (5) that is already in the bone tissue, and uses it as transfer molding for making the plaster model.

In this step, the practitioner removes the multifunctional prosthetic component (4) of the model and performs its section through a commonly used disc laboratory technique, obtaining the prismatic head (4.1), which is discarded, and the prosthetic pillar (4.2), which returns the model for the adaptation of the cylinder, which is fitting conducted through a click on their internal projections.

Once adapted on the cylinder, which has external grooves for retaining the resin, the prosthesis is constructed by means of currently known techniques.

At the end, the prosthetic pillar (4.2) and the cylinder/prosthesis assembly are removed from the model and positioned over the implant (5) in the mouth, where the prosthetic pillar (4.2) is fixed to the implant (5) with a fixing screw (3), and the cylinder/prosthesis assembly is again embedded in the prosthetic pillar (4.2) with one click, associated with or without the cementing process. The orientation of the positioning cylinder/and the temporary prosthesis in the pillar (4.2) and anti-rotational fitting of the prosthesis are guaranteed by the vertical internal convex ridges of the cylinder.

This innovation is not limited to the aspects, examples and representations discussed or shown herein, and must be understood in its widest scope. Many modifications and other representations will come to the mind of those skilled in the area to which this innovation belongs, having the benefit of the teachings presented in the foregoing descriptions and annexed drawings. Furthermore, it is to be understood that the innovation is not limited to the specific forms disclosed, and that modifications and other forms are understood as being included within the scope of the annexed claims. Although specific terms are employed herein, these are used only in a generic and descriptive form and with a limiting purpose.

The invention claimed is:

1. A multifunctional prosthetic component comprising:
   a prismatic head having one or more smaller faces and one or more larger faces;
   one or more grooves below the prismatic head;
   a prosthetic pillar having one or more concave vertical external grooves, the one or more grooves being aligned or linked with the one or more larger faces of the prismatic head;
   a channel above a base of the prosthesis; and
   an internal cavity having one or more internal faces, wherein the one or more internal faces are indexed with the one or more larger faces of the prism head, and with the one or more external vertical concave grooves of the prosthetic pillar, wherein the one or more internal faces are configured to index with one or more external faces of a dental implant.

2. The multifunctional prosthetic component of claim 1, wherein the one or more smaller faces are hexagonal in shape.

3. The multifunctional prosthetic component of claim 1, wherein the one or more larger faces are triangular in shape.

4. The multifunctional prosthetic component of claim 1, wherein the one or more smaller faces are hexagonal in shape and the one or more larger faces are triangular in shape.

5. The multifunctional prosthetic component of claim 1, wherein the one or more concave vertical external grooves are aligned with the one or more larger faces of the prismatic head.

6. The multifunctional prosthetic component of claim 1, wherein the one or more concave vertical external grooves are linked with the one or more larger faces of the prismatic head.

7. The multifunctional prosthetic component of claim 1, wherein the internal cavity is hexagonal in shape, and wherein the internal faces of the hexagonal cavity are configured to index the external faces of an external hexagon on a dental implant.

8. A dental implant system, the system comprising:
   a multifunctional prosthetic component, the multifunctional prosthetic component comprising:
   a prismatic head having one or more smaller faces and one or more larger faces;
   one or more grooves below the prismatic head;
   a prosthetic pillar having one or more concave vertical external grooves, the one or more grooves being aligned or linked with the one or more larger faces of the prismatic head;
   a channel above a base of the prosthesis; and
   an internal cavity having one or more internal faces, wherein the one or more internal faces are indexed with the one or more larger faces of the prism head, and with the one or more external vertical concave grooves of the prosthetic pillar, wherein the one or more internal faces are configured to index with one or more external faces of a dental implant; and
   a cylinder configured to be adapted onto the multifunctional prosthetic component, the cylinder having one or more internal protrusions, one or more external grooves, and one or more convex vertical internal ridges.

9. The dental implant system of claim 8, further comprising:

a plastic cover having a channel shaped clamp for accurate fixation of the multifunctional prosthetic component and a cylindrical rod configured to allow fixing of an O-ring of an installation key.

10. The dental implant system of claim 9, further comprising a screw, wherein the screw is configured to fix the multifunctional prosthetic component onto a dental implant, allowing the component's use as a prosthetic pillar.

11. The dental implant system of claim 10, further comprising a dental implant, the implant having one or more external faces.

12. The dental implant system of claim 11, further comprising an installation key, the installation key having an O-ring.

13. The dental implant system of claim 12, wherein the one or more smaller faces are hexagonal in shape, wherein the one or more larger faces are triangular in shape, wherein the internal cavity is hexagonal in shape, and wherein the internal faces of the hexagonal cavity are configured to index the external faces of an external hexagon on a dental implant.

14. The method of use of the dental implant system of claim 12, the method comprising:
transporting the plastic cover, the multifunctional prosthetic component and the implant to the bone tissue through the installation key, wherein the O-ring of the key is coupled with the cylindrical rod of the plastic cover fixed to the multifunctional prosthetic component;
applying torque on the one or more smaller faces of the prismatic head of the multifunctional prosthetic component;
inserting the implant through a connection coupled to a ratchet torque wrench supported on the smaller faces of the prismatic head, allowing for the exact fixing of the assembly;
removing the multifunctional prosthetic component of the implant allocated to the bone tissue;
using the multifunctional prosthetic component to transfer the molding for making the plaster model;
sectioning the multifunctional prosthetic component to separate the prismatic head from the prosthetic pillar;
adapting the prosthetic pillar to the cylinder by means of the fitting to the one or more internal projections;
constructing the prosthesis temporarily using the prosthetic pillar to form a cylinder/prosthesis group;
positioning the prosthetic pillar and cylinder/prosthesis group on the implant in the mouth, wherein the prosthetic pillar is fixed to the implant with a fixing screw;
orienting the position of the cylinder/prosthesis group on the prosthetic pillar by the one or more convex internal vertical ridges of the cylinder.

15. The method of claim 14, wherein the molding is transferred with the plastic cover in position.

16. The method of claim 14, wherein the molding is transferred without the plastic cover in position.

* * * * *